United States Patent [19]

Nose et al.

[11] Patent Number: 4,887,897
[45] Date of Patent: Dec. 19, 1989

[54] EYE EXAMINING APPARATUS

[75] Inventors: Noriyuki Nose, Tokyo; Yukichi Niwa, Kanagawa, both of Japan

[73] Assignee: Canon Kabushiki Kaisha, Tokyo, Japan

[21] Appl. No.: 306,225

[22] Filed: Feb. 3, 1989

Related U.S. Application Data

[63] Continuation of Ser. No. 94,895, Sep. 10, 1987, abandoned.

[30] Foreign Application Priority Data

Sep. 16, 1986 [JP] Japan ................. 61-217817

[51] Int. Cl.⁴ .......................... A61B 3/02; A61B 3/10
[52] U.S. Cl. .................................. 351/233; 351/234; 351/235; 351/211

[58] Field of Search ............... 351/233, 234, 235, 41, 351/211, 216, 217, 218, 223, 227, 228, 229, 230, 231

[56] References Cited

U.S. PATENT DOCUMENTS

| 4,403,840 | 9/1983 | Okun | 351/41 |
| 4,418,990 | 12/1983 | Gerber | 351/41 |
| 4,697,598 | 10/1987 | Bernard | 351/205 X |

Primary Examiner—Rodney B. Bovernick
Attorney, Agent, or Firm—Fitzpatrick, Cella, Harper & Scinto

[57] ABSTRACT

An eye examining apparatus has an eye examining lens of an elastic material opposed to an eye to be examined, and control means for causing the marginal portion of the eye examining lens to protrude or sink to thereby change the lens surface of the eye examining lens.

13 Claims, 3 Drawing Sheets

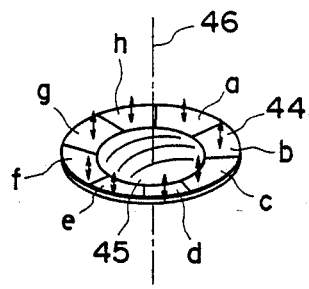
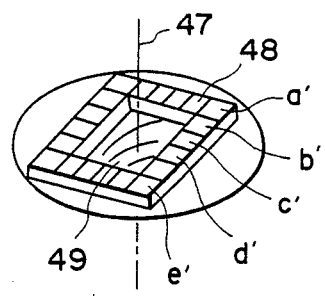
F I G. 7A          F I G. 7B
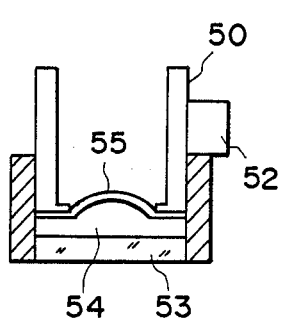
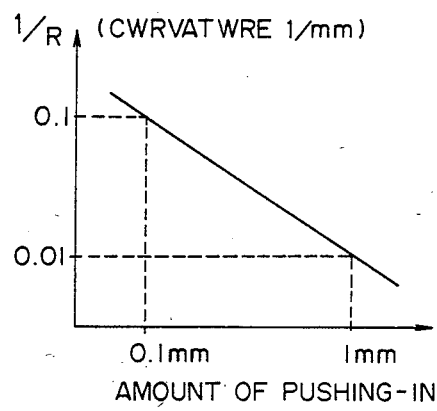
F I G. 8          F I G. 9
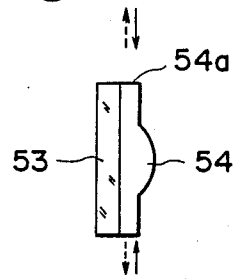
F I G. 10

EYE EXAMINING APPARATUS

This application is a continuation of application Ser. No. 07/094,895 filed Sept. 10, 1987 now abandoned.

BACKGROUND OF THE INVENTION

1. Field of the Invention

The present invention relates to an eye examining apparatus for effecting eye examination by selectively changing over the refractive power of a lens.

2. Related Background Art

Eye examining apparatuses for finding the optimum degrees of spectacles are well known. An eye examining apparatus effects not only the measurement of the degree of eye refraction, the degree of astigmatism and the axial direction of the human eye, but also the measurement of examination of presbyopia, heterophoria, vergence, divergence and balance of both eyes. To make these examinations possible, the eye examining apparatus according to the prior art has an optical system of such structure as shown of on FIG. 1 of the accompanying drawings. FIG. 1 shows an optical system in the eye examining apparatus for measuring only one of left and right eyes. The actual eye examining apparatus provides two optical systems as shown in FIG. 1 and effects the examination of left and right eyes. In FIG. 1, reference numeral 1 designates an auxiliary lens plate, reference numeral 2 denotes a second spherical lens plate, reference numeral 3 designates a first spherical lens plate, reference numeral 4 denotes a second cylindrical lens plate, reference numeral 5 designates a first cylindrical lens plate, reference numeral 6 denotes an accessory lens, reference numeral 7 designates a rotatable prism, reference numeral 8 denotes a mabdox rod, reference numeral 9 designates a cross cylinder, and reference numeral 10 denotes an eye examining lens chamber. The members 7, 8 and 9 will hereinafter be referred to as the auxiliary magnifiers. The eye examining lens chamber contains therein several disks having a number of eye examining lenses planted thereon as shown in FIG. 1. The auxiliary lens plate 1 (having a prism, a pin-hole, etc.), the second spherical lens plate 2, the first spherical lens plate 3 (for measuring distance visibility), the second cylindrical lens plate 4 and the first cylindrical lens plate 5 (for measuring the degree of astigmatism) overlap one another from the examinee side, and an arbitrary combination of these can be quickly brought out to an eye examining window by rotating the disks having the eye examining lenses planted thereon. The total degree of diopter may be displayed by a simple calculation.

The aforementioned three measuring plates called the auxiliary magnifiers are installed on the front face of the eye examining window, and they can be moved into and out of the window simultaneously or one by one. Reference numeral 7 designates a rotatable prism for measuring heterophoria, and this prism continuously provides a variation in declination by the rotation of two prisms in opposite directions. The mabdox rod 8 is used for the measurement of heteropheria. The cross cylinder 9 comprises, for example, the area of cylindrical lenses of ±0.25 diopter made orthogonal to each other, and is a very useful device for the precise measurement of astigmatism, the determination of presbyopia and other purposes. By the apparatus of the construction as described above, it is possible to measure the farsightedness and near-sightedness (the degree of sphericity), astigmatism, astigmatic axis, heterophoria, vergence, divergence, pupil distance etc.

In the prior art, however, a number of eye examining lenses are prepared from the necessity of coping with diversified visual powers and it is necessary to change these lenses in succession. This has led to a bulky expensive and cumbersome apparatus. Also, the large degree of mechanical movement during the change-over has led to the disadvantage that much time is required for the change-over. Since a number of eye examining lenses are interchangeably set in a limited installation space, the lens aperture of the eye examining lenses must avoidably be made small, and this has led to the disadvantage that so-called mechanical myopia is liable to occur.

Furthermore, in the prior art, a number of lenses have been set in the direction of the optic axis and therefore, even if a predetermined one of these lenses is changed over at a predetermined step (e.g. of 0.25 diopter each) to vary the refractive power thereof, the refractive power is not varied at the step of 0.25 diopter since as the whole system is provided with a number of lenses.

Also, in the prior art, a predetermined eye examining lens is entirely eliminated during the changeover, and this may lead to the possibility that the adjustment power of the eye to be examined will change.

SUMMARY OF THE INVENTION

It is an object of the present invention to eliminate the above-noted disadvantages peculiar to the prior art and to provide an eye examining apparatus which is capable of quickly and simply examining the information of an eye to be examined without preparing a number of eye examining lenses.

It is another object of the present invention to provide an eye examining apparatus which is capable of accurately examining the information of the eye to be examined by making the aperture of an eye examining lens great and making it difficult for mechanical myopia to occur.

It is still another object of the present invention to provide an eye examining apparatus which is capable of measuring the information of the eye to be examined by a measuring system through an eye examining lens opposed to the eye to be examined, and varying the refractive power of the eye examining lens in comformity with the result of the measurement by the measuring system to thereby accomplish automatic examination.

BRIEF DESCRIPTION OF THE DRAWINGS

FIGS. 2 to 7 show embodiments of the present invention.

FIGS. 8 and 9 illustrate the detection of the actual shape of an optical element.

FIG. 10 shows an embodiment in which a pressure is applied to a cross surface perpendicularly to the optic axis.

DESCRIPTION OF THE PREFERRED EMBODIMENTS

Figure 1:
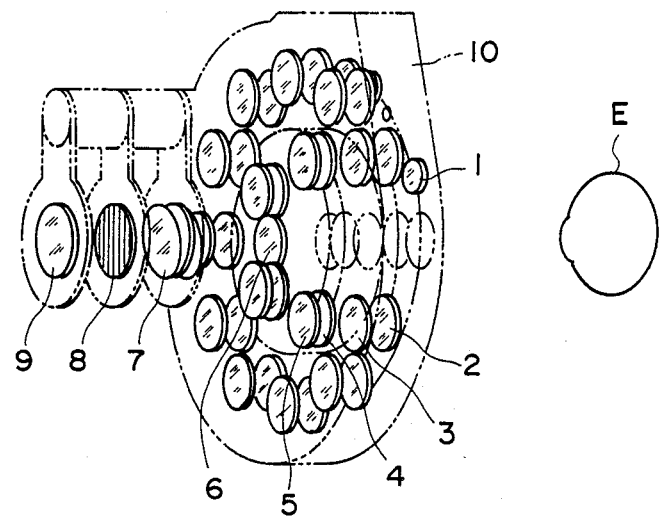
FIG. 1 shows an example of the prior art.
Figure 2:
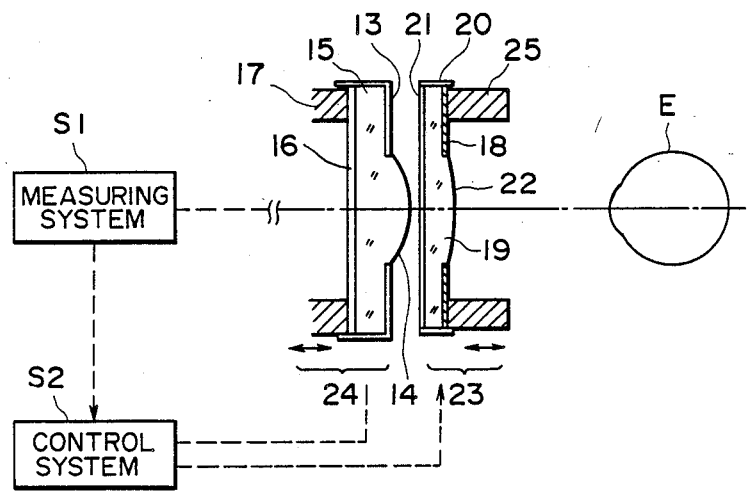

Some embodiments of the present invention will hereinafter be described. In FIG. 2, a lens structure for eye examination generally comprises lens structures 24 and 23. The lens structure 24 is an optical element portion which provides a light refracting power and a prism effect, and the lens structure 23 is a portion which provides asymmetry of refractive power. The lens structures 23 and 24 are capable of automatically changing the refractive power to a predetermined refractive power in conformity with the result of the measurement by an unconscious type refractive power measuring system S1 (for example, a conventional refractive power measuring system known from Japanese Laid-Open patent application No. 161031/1981) through a control system S2.

In FIG. 2, the optical surface 14 of an elastic member 15 is in contact with an opening 13 and has its radius of curvature variable by the amount of push-in through the plate 16 of a push-in member 17. If the amount of push-in of the push-in member 17 differs from location to location in the annular marginal portion thereof, the lens structure 24 will exhibit a nature equivalent to the optical characteristic having a wedge-shaped prism as a base. Thus, basically, the lens structure 24 is capable of continuously varying the refractive power. Since the push-in member 17 holds down the marginal portion of the lens surface, the vertex of the lens surface is not greatly varied and the position of the principal point of the lens hardly changes.

Figure 3:
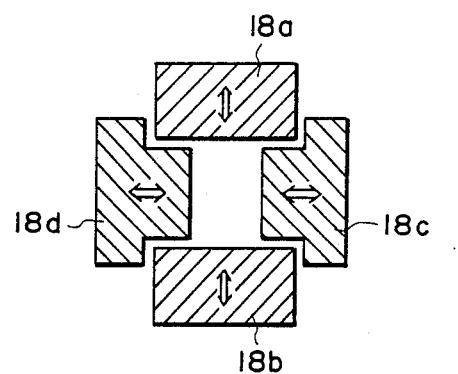

In contrast, the lens structure 23 has a structure which creates asymmetry of refractive power, and is used for the measurement of astigmatism. That is, the lens structure 23 is set so that it is possible to provide an optical effect equivalent to a state in which two cylindrical lenses cross each other and overlap each other. To cause the lens structure 23 to create such an effect, the surface 22 of an elastic member 19 received by plates 20 and 21 is pushed and deformed by a push-in member 25 through members 18a–18d forming a rectangular opening as shown in FIG. 3 (i.e., an opening having different opening widths in directions orthogonal to each other). In that case, the lengths of the longer side and shorter side of the rectangle are correlated with the curvatures of a cylindrical lens and a toric lens and therefore, the members 18a–18d are movable so that the size of the rectangular opening is varied. Thereby the degree of astigmatism can be set freely.

Figure 4A:
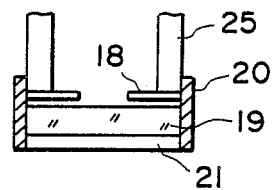
Figure 4B:
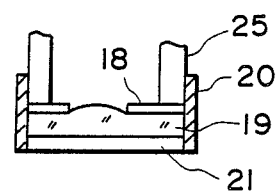

As shown in FIGS. 4A and 4B the surface of the elastic member 19 is flat before an opening member 18 is urged against it, and may create a curvature by the opening member 18 being urged against it. The plate 21 is a transparent member such as glass. The lens structure 23 is made rotatable with respect to the optic axis, and by reading the angle of rotation thereof, it is possible to measure the astigmatic axis. When the shape of the opening has been determined, the absolute value of the curvature is determined by how deeply the opening is pushed in relative to the elastic member, and if the amount of push-in is great, the radius of curvature becomes smaller.

Figure 5:
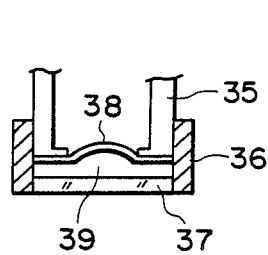

In the above-described embodiment, the elastic member is shown as a structure formed of a single material, whereas it need not always be formed of a single material, but may be of two-layer structure as shown in FIG. 5. In FIG. 5, reference numerals 38 and 39 designate elastic members different in rigidity and layered one upon the other. For example, the elastic member 38 is greater in rigidity than the elastic member 39. Reference numeral 37 denotes a transparent member formed of a material such as glass.

Now, the lens structure 24 in FIG. 2 has its surface shape, in a state in which it is not subjected to the deformation of the elastic member by the opening (hereinafter referred to as the initial stage), made into a convex shape and further deformed into a convex shape of sharper curvature, or has its initial shape made into a concave shape and can have the curvature of the concave shape varied so as to become smaller by pressure-deforming the elastic member.

Figure 6:
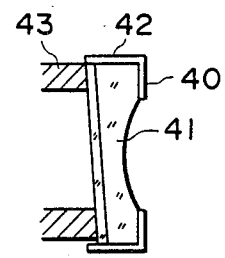

In addition to the variation in refractive power, a prism-like wedge effect can be independently created, and an example of such case is shown in FIG. 6. When as shown in FIG. 6, an elastic member 41 is compressed to vary the curvature thereof, if the amount of push-in of a member 43 for pushing a transparent material 42 is changed depending on the location in the annulus, the lip angle of the prism effect can be arbitrarily set in addition to the variation in curvature.

For example, in the case of a concave lens whose initial surface shape has a radius of curvature of 50 mm, it has been empirically confirmed that where the lens has a center thickness of 4 mm and a two-layer structure as shown in FIG. 5 and the effective diameter thereof is 20 mm, if the amount of push-in of the push-in member is changed by 0.3 mm, the radius of curvature of the lens changes by about 10 diopters.

Now, besides the opening-forming member shown in FIG. 3, there may be conceived an annular opening-forming member divided into several portions which are capable of being independently pushed and pulled in the direction of the optic axis. Such examples are shown in FIG. 7. In FIG. 7A, reference characters a–h designate the divided portions of an annular opening-forming member 44 which are independently displaceable in the direction of the optic axis 46. Reference numeral 45 denotes the optical surface of the elastic member. In FIG. 7B, there is shown an example in which a rectangular opening is divided into several portions which are capable of being independently pushed and pulled in the direction of the optic axis. In both of the examples shown in FIGS. 7A and 7B, setting is possible so that the surface of the elastic member has a toric shape by changing the amount of push and pull of each portion and providing a distribution. For example, in FIG. 7A, the values of the portions c and g may be made greatest for the same amount of push-in and the values of the portions a and e may be made smallest for the same amount of push-in. The number of divisions of the annular opening-forming member and the rectangular opening-forming member may be arbitrary, but preferably, a greater number of divisions may lead to finer push-in distribution of the opening.

The layers of the elastic member are not limited to two layers, but may be of multi-layer structure of three or more layers, and the thicknesses of the layers need not be uniform but may have a thickness distribution. Also, irrespective of the multi-layer structure or the single structure, the elastic member may have three-dimensionally distributed rigidity.

The elastic member used in the present invention may be of a material (such as silicone rubber) having the property (elasticity) of causing deformation when a force is applied to the material and recovering from the deformation when the force is removed as long as the applied force is not very great (within the limit of elasticity). The method of deforming the optical surface in the opening portion of the elastic member can utilize not only an extraneous force, but also a variation in volume by thermal expansion and contraction or sol⇌gel change by the use of said material. Also, the member having an opening for forming the optical surface of the elastic member may be one provided with a flat opening or, where the elastic member is used while being contained in a container, one having an opening provided in at least one wall of the container. This opening differs depending on the required optical effect, but generally opens circularly to form a concave-convex lens of variable focal length. Also, an opening may be provided in the form of a rectangular slit to thereby form a cylindrical lens and a toric lens. The optical element formed by these openings can have its shape varied arbitrarily by an extraneous force applied to the elastic member or a variation in the volume of the elastic member, and the degree thereof can be controlled by feedback while detecting any change in the actual shape.

This opening can also be constituted by a piezoelectric element such as a cylinder type piezo, whereby remarkable compactness of the element can be realized. Further, by a variation in the area of the opening, the degree of protrusion or the degree of sinking of the optical surface of the elastic member formed in the opening can be changed to obtain a desired optical characteristic, and by changing the configuration of the opening, for example, by changing the circular opening into an elliptical shape or a rectangular shape, there can also be provided a toric lens or a cylindrical lens.

Detection of the actual shape of the optical element will now be described. In FIG. 8, there is shown an example in which a measuring machine detects how deeply the opening has been pushed in relative to the elastic member. Of course, this example is applicable to the automatized system shown in FIG. 2. A moving member 50 having an opening is moved so as to push in a lens 54 of variable focal length placed on a glass plate 53 and formed of silicone rubber or the like and the amount of movement thereof is measured by a measuring machine 52. There is a substantially linear relation as shown in FIG. 9 between the curvature of the lens surface 55 of the lens 54 of variable focal length and the amount of movement (the amount of push-in) of the moving member 50, and such a relation is prestored in a computer.

In the present invention, as previously described, the vertex of the lens surface is not greatly changed by changing the marginal portion of the lens and the position of the principal point of the lens hardly changes and therefore, the relation between the curvature of the lens surface and the amount of push-in of the moving member may be expressed by a simple function.

The measuring machine 52 may be, for example, a magnescale or an optical type interference measuring machine. As regards the cylindrical lens system, the power of the lens is determined by the longitudinal and lateral widths of the opening in the moving member 50 and the measurement of the amount of push-in of the moving member 50.

The above-described embodiment is such that the lens is deformed by applying a pressure in the direction of the optic axis of the lens, but alternatively, as shown in FIG. 10, the lens may be deformed by applying a pressure to the cross or edge surface 54a of the lens 54 of variable focal length placed on the glass plate 53, in a direction perpendicular to the optic axis.

As described above, according to the present invention, eye examination can be accomplished by a single eye examining lens and the apparatus is made compact, and also the change-over of the refractive power can be accomplished quickly. Moreover, the aperture of the eye examining lens can be made great to make it difficult for mechanical myopia to occur. Also, it is possible to vary the refractive power exactly by a predetermined step. Further, the eye examining lens is normally opposed to the eye to b examined and therefore, it is considered that the variation in the adjusting power of the eye to be examined is almost null.

We claim:

1. An eye examining apparatus comprising:
   an eye examining lens of an elastic material opposed to an eye to be examined;
   control means for causing a marginal portion of said eye examining lens to protrude or sink to thereby change a lens surface of said eye examining lens;
   said control means including an opening member having an opening operably associated with a central portion of said eye examining lens such that when said opening member is moved in the direction of an optic axis of said eye examining lens the surface of the marginal portion of said lens is deformed; and
   a measuring machine for measuring the amount of movement of said opening member in the direction of the optic axis.

2. An eye examining apparatus comprising:
   an eye examining lens of an elastic material opposed to an eye to be examined;
   control means for causing a marginal portion of said eye examining lens to protrude or sink to thereby change a lens surface of said eye examining lens;
   said control means including an opening member having an opening operably associated with a central portion of said eye examining lens such that when said opening member is moved in the direction of an optic axis of said eye examining lens the surface of the marginal portion of said lens deforms; and
   said opening member having a piezo-electric element.

3. An eye examining apparatus comprising:
   an eye examining lens of an elastic material opposed to an eye to be examined;
   control means for causing a marginal portion of said eye examining lens to protrude or sink to thereby change a lens surface of said eye examining lens;
   said eye examining lens including a first lens for providing a refractive power symmetrical with respect to an optic axis of said eye examining lens, and a second lens for providing a refractive power asymmetrical with respect to the optic axis of said eye examining lens.

4. An eye examining apparatus comprising:
   an eye examining lens of an elastic material opposed to an eye to be examined;
   a measuring system for measuring the information of the eye to be examined through said eye examining lens;
   control means for causing a marginal portion of said eye examining lens to protrude or sink in conformity with the result of the measurement by said measuring system to thereby change a lens surface of said eye examining lens;
   said control means including an opening member having an opening operably associated with a central portion of said eye examining lens such that when said opening member is moved in the direction of an optic axis of said eye examining lens the surface of the marginal portion of said lens is deformed; and
   a measuring machine for measuring the amount of movement of said opening member in the direction of the optic axis.

5. An eye examining apparatus comprising:
an eye examining lens of an elastic material opposed to an eye to be examined;
a measuring system for measuring the information of the eye to be examined through said eye examining lens;
control means for causing a marginal portion of said eye examining lens to protrude or sink in conformity with the result of the measurement by said measuring system to thereby change the lens surface of said eye examining lens;
said control means including an opening member having an opening operably associated with said eye examining lens such that when said opening member is moved in the direction of an optic axis of said eye examining lens the surface of a marginal portion of said lens is deformed; and
said opening member including a piezo-electric element.

6. An eye examining apparatus comprising:
an eye examining lens of an elastic material opposed to an eye to be examined;
a measuring system for measuring the information of the eye to be examined through said eye examining lens;
control means for causing a marginal portion of said eye examining lens to protrude or sink in conformity with the result of the measurement by said measuring system to thereby change a lens surface of said eye examining lens; and
said eye examining lens including a first lens for providing a refractive power symmetrical with respect to an optic axis of said eye examining lens, and a second lens for providing a refractive power asymmetrical with respect to the optic axis.

7. An eye examining apparatus comprising:
an eye examining lens of an elastic material opposed to an eye to be examined;
control means for causing a marginal portion of said eye examining lens to protrude or sink to thereby change a lens surface of said eye examining lens;
said control means including an opening member having an opening associated with a central portion of one side of said eye examining lens and an opposing member associated with another side of said eye examining lens such that when said opening member and said opposing member are relatively moved in the direction of an optic axis of said eye examining lens, the surface of the marginal portion of said lens is deformed; and
a measuring means for measuring the amount of movement in the direction of said optic axis.

8. An eye examining apparatus comprising:
an eye examining lens of an elastic material opposed to an eye to be examined;
a measuring system for measuring the information of the eye to be examined through said eye examining lens;
control means for causing a marginal portion of said eye examining lens to protrude or sink in conformity with the result of the measurement by said measuring system to thereby change a lens surface of said eye examining lens;
said control means including an opening member having an opening associated with a central portion of one side of said eye examining lens and an opposing member associated with another side of said eye examining lens such that when said opening member and said opposing member are relatively moved in the direction of an optic axis of said eye examining lens, the surface of the marginal portion of said lens is deformed; and
a measuring means for measuring the amount of movement in the direction of said optic axis.

9. An eye examining apparatus comprising:
an eye examining lens of an elastic material opposed to an eye to be examined;
control means for causing a marginal portion of said eye examining lens to protrude or sink to thereby change a lens surface of said eye examining lens;
said control means including an opening member having an opening associated with a central portion of one side of said eye examining lens and an opposing member associated with another side of said eye examining lens such that when said opening member and said opposing member are relatively moved, the surface of the marginal portion of said lens is deformed; and
a measuring means for measuring the amount of movement in the direction of the optic axis.

10. An eye examining apparatus according to claim 9, wherein the direction relatively moved is perpendicular to the direction of the optic axis of said eye examining lens.

11. An eye examining apparatus comprising:
an eye examining lens of an elastic material opposed to an eye to be examined;
a measuring system for measuring the information of the eye to be examined through said eye examining lens;
control means for causing a marginal portion of said eye examining lens to protrude or sink in conformity with the result of the measurement by said measuring system to thereby change a lens surface of said eye examining lens;
said control means including an opening member having an opening associated with a central portion of one side of said eye examining lens and an opposing member associated with another side of said eye examining lens such that when said opening member and said opposing member are relatively moved, the surface of the marginal portion of said lens is deformed; and
a measuring means for measuring the amount of movement in the direction of the optic axis.

12. An eye examining apparatus according to claim 11, wherein the direction relatively moved is perpendicular to the direction of the optic axis of said eye examining lens.

13. An eye examining apparatus comprising:
an eye examining lens of an elastic material opposed to an eye to be examined;
control means for causing a marginal portion of said eye examining lens to protrude or sink to thereby change a lens surface of said eye examining lens;
said control means including an opening member having an opening operably associated with a central portion of said eye examining lens such that when said opening member is moved, the surface of the marginal portion of said lens deforms; and
said opening member having a piezo-electric element.

* * * * *